(12) United States Patent
Jochum et al.

(10) Patent No.: US 12,164,982 B2
(45) Date of Patent: Dec. 10, 2024

(54) METHOD FOR LABELLING PRODUCTS WITH AN OPTICAL SECURITY FEATURE WITH A TEMPORAL DIMENSION

(71) Applicant: FRAUNHOFER-GESELLSCHAFT ZUR FÖRDERUNG DER ANGEWANDTEN FORSCHUNG E. V., Munich (DE)

(72) Inventors: Tobias Jochum, Hamburg (DE); Jan Niehaus, Hamburg (DE)

(73) Assignee: FRAUNHOFER-GESELLSCHAFT ZUR FÖRDERUNG DER ANGEWANDTEN FORSCHUNG E. V., Munich (DE)

( * ) Notice: Subject to any disclaimer, the term of this patent is extended or adjusted under 35 U.S.C. 154(b) by 0 days.

(21) Appl. No.: 18/037,873

(22) PCT Filed: Nov. 23, 2021

(86) PCT No.: PCT/EP2021/082595
§ 371 (c)(1),
(2) Date: May 19, 2023

(87) PCT Pub. No.: WO2022/112209
PCT Pub. Date: Jun. 2, 2022

(65) Prior Publication Data
US 2023/0409844 A1    Dec. 21, 2023

(30) Foreign Application Priority Data
Nov. 26, 2020    (DE) .......................... 102020131382.9

(51) Int. Cl.
*G06K 1/12*    (2006.01)
*A61L 2/28*    (2006.01)
(Continued)

(52) U.S. Cl.
CPC ................ *G06K 1/123* (2013.01); *A61L 2/28* (2013.01); *B41M 3/144* (2013.01);
(Continued)

(58) Field of Classification Search
CPC .......... G06K 1/123; B42D 25/378; A61L 2/28
(Continued)

(56) References Cited

U.S. PATENT DOCUMENTS 5,282,894 A    2/1994    Albert et al.
5,542,971 A    8/1996    Auslander et al.
(Continued)

FOREIGN PATENT DOCUMENTS

DE           10346632 A1    5/2005
DE        102015219400 A1    4/2017
(Continued)

OTHER PUBLICATIONS

International Search Report and Written Opinion with English Translation for Application No. PCT/EP2021/082595 mailed on Feb. 25, 2022, 18 pages.
(Continued)

*Primary Examiner* — Allyson N Trail
(74) *Attorney, Agent, or Firm* — Lowenstein Sandler LLP

(57) ABSTRACT

The present invention is based on a method for marking products using two or more ink formulations, each containing one or more photoluminescent dyes emitting radiation in the range of 380-3000 nm under photon excitation and distinguished by different fluorescence lifetimes, for storing information in serialization and/or track & trace systems and for document security.

20 Claims, 3 Drawing Sheets

0 ns 25 ns 100 ns

(51) Int. Cl.
  *B41M 3/14* (2006.01)
  *B42D 25/378* (2014.01)
  *C09D 11/037* (2014.01)
  *C09D 11/328* (2014.01)
  *C09D 11/50* (2014.01)
  *G01N 21/64* (2006.01)
  *G06K 19/06* (2006.01)

(52) U.S. Cl.
  CPC .......... *B42D 25/378* (2014.10); *C09D 11/037* (2013.01); *C09D 11/328* (2013.01); *C09D 11/50* (2013.01); *G01N 21/6408* (2013.01); *G01N 21/6428* (2013.01); *G01N 21/6456* (2013.01); *G06K 19/06037* (2013.01); *G06K 19/0614* (2013.01); *G01N 2021/6439* (2013.01)

(58) Field of Classification Search
  USPC .......................................................... 235/494
  See application file for complete search history.

(56) References Cited

U.S. PATENT DOCUMENTS

| | | | |
|---|---|---|---|
| 5,665,151 A | 9/1997 | Escano et al. | |
| 5,990,197 A | 11/1999 | Escano et al. | |
| 6,692,031 B2 | 2/2004 | McGrew | |
| 7,070,646 B2 | 7/2006 | Campbell | |
| 8,700,501 B2 | 4/2014 | Løken | |
| 8,898,077 B2 | 11/2014 | Davis, Jr. | |
| 9,027,147 B2 | 5/2015 | Simske et al. | |
| 9,382,432 B1 | 7/2016 | McDaniel | |
| 10,119,071 B2 | 11/2018 | Lewis | |
| 10,140,494 B1* | 11/2018 | Lawandy | G06V 20/95 |
| 11,900,497 B1* | 2/2024 | Falkenstern | G06T 1/0028 |
| 2007/0210574 A1 | 9/2007 | Schwenk et al. | |
| 2009/0096871 A1 | 4/2009 | Kuwano et al. | |
| 2013/0161395 A1 | 6/2013 | Tian et al. | |
| 2013/0161396 A1 | 6/2013 | Ming et al. | |
| 2014/0021369 A1 | 1/2014 | Rapoport et al. | |
| 2016/0012465 A1* | 1/2016 | Sharp | G06Q 20/321 705/14.17 |
| 2017/0082542 A1* | 3/2017 | McDaniel | G01N 21/63 |
| 2019/0226990 A1 | 7/2019 | Reinhart et al. | |
| 2019/0304231 A1 | 10/2019 | Milos-Schouwink | |
| 2019/0358990 A1 | 11/2019 | Rauscher et al. | |
| 2020/0003772 A1* | 1/2020 | Harel | G01N 33/5308 |
| 2020/0198384 A1* | 6/2020 | Bollstrom | B41M 3/006 |
| 2021/0213771 A1 | 7/2021 | Deckenbach et al. | |
| 2021/0287230 A1* | 9/2021 | Decoux | B42D 25/21 |
| 2022/0292276 A1* | 9/2022 | Lee | G06K 7/10732 |
| 2022/0402205 A1* | 12/2022 | Hinch | B33Y 10/00 |

FOREIGN PATENT DOCUMENTS

| | | |
|---|---|---|
| DE | 102008050768 C5 | 11/2017 |
| DE | 102016011180 A1 | 3/2018 |
| DE | 102018102015 A1 | 8/2019 |
| DE | 102018007096 A1 | 3/2020 |
| DE | 102019216003 A1 | 4/2021 |
| EP | 0933407 A1 | 8/1999 |
| EP | 3301655 A1 | 4/2018 |
| EP | 2100277 B1 | 1/2019 |
| JP | 2019527869 A | 10/2019 |
| JP | 2020002030 A | 1/2020 |
| WO | 9818871 A1 | 5/1998 |
| WO | 03038003 A1 | 5/2003 |
| WO | 2008064644 A2 | 6/2008 |
| WO | 2013188927 A1 | 12/2013 |

OTHER PUBLICATIONS

German Search Report for Application No. PCT/EP2021/082595 mailed on Jul. 21, 2021, 6 pages.

Reasons for Rejection for Japanese Patent Application No. 2023-529046, translated Aug. 6, 2024, 16 pages.

* cited by examiner

METHOD FOR LABELLING PRODUCTS WITH AN OPTICAL SECURITY FEATURE WITH A TEMPORAL DIMENSION

CROSS-REFERENCE TO RELATED APPLICATION(S)

The present application is a national phase entry under 35 U.S.C. § 371 of International Application No. PCT/EP2021/082595, filed on Nov. 23, 2021, which claims priority to German Patent (DE) application No. 102020131382.9 filed on Nov. 26, 2020. The contents of these applications are hereby incorporated by reference herein in their entirety.

The present invention is based on a method for marking products using two or more ink formulations, each containing one or more photoluminescent dyes that emit radiation in the range of 380-3000 nm under photon excitation and differ in photoluminescence lifetimes, for information storage, in serialization and/or track & trace systems, and for document security.

TECHNICAL BACKGROUND

Product counterfeiting causes worldwide economic damage of several hundred billion US dollars. In Europe alone, product counterfeiting causes economic damage of more than 80 billion euros. The range of counterfeit products is immense. Cosmetics, watches, tobacco and medical products are increasingly being counterfeited. The pharmaceutical and tobacco industries—due to EU requirements (2011/62/EU and 2014/40 EU)—have introduced a serialization system in 2019 to monitor their products. In this process, each product package is equipped with a special, unique code and this is stored in a central database. Several problematic scenarios arise in the process:

Hacking the database. It is important to note that no IT system can be fully protected against hacking by third parties. The hackers can either save/add their own codes to the central database or match the unique codes of the other companies. Thus, it is no longer possible to verify which product is a counterfeit and which product is the original.

Passing the codes to third parties. The unique codes can be passed on to third parties by personnel. They can then print the codes on the counterfeit products so that they are considered "genuine" according to the database.

Transferring the codes to another package. Once the code is transferred from the original packaging to the duplicate packaging and the original packaging is discarded, counterfeit preparations can be sold as genuine products. This fraud is difficult to trace because the database system confirms that the product at hand is not a counterfeit. This risk scenario would be conceivable, for example, in the repackaging of stolen products/medicines and in the case of illegal trade in products on the Internet or in smuggled goods.

Due to these three critical points, it is very important to develop/design a "cyber-physical system (CPS)"; i.e. a combination of digital and physical features.

CPS are also needed for application in Industry 4.0 and Logistics 4.0 (supply chain security). In Industry 4.0, every work process is to be digitized and networked. Machines will take over the respective jobs of tomorrow. This is only possible if a high level of security can be guaranteed. Machines must be able to trust machines. This is achieved by equipping each end product (including subproducts, tools, processes . . . ) of a work step with an identity (a la track & trace). However, there are differences in identities. There are 3 types of identities:

Identity (ID): e.g.: QR code
Unique identity: e.g.: QR code with serial number
Secure identity: e.g. QR code with second factor Regarding anti-counterfeiting of products, two main competing solutions have been worked on in recent years, namely Track & Trace and authentication solutions, especially on an optical basis.

Track & Trace programs (U.S. Pat. Nos. 9,027,147; 8,898,007; US 2009/0096871; U.S. Pat. No. 8,700,501) are used to ensure the unambiguous tracking and tracing of all process steps in the production and supply chain. They also enable comprehensive control options for the manufacturer and transparency for the consumer, as the locations and paths of products and documents can be documented without gaps. Information stores are needed for this purpose. Depending on the information memory, a distinction is made between a 1-dimensional barcode (bar dot), 2-dimensional barcode (QR code), 3-dimensional barcode (colored barcode EP 2100277B1) and the 4-dimensional barcode (colored barcode+temporal component US 2013/0161395 A1). In the currently established 4D barcode, a colored pattern is changed in time. However, this type is not printable because the temporal change requires a display with a memory unit. It is therefore not to be used on product packaging.

For authentication solutions, the interaction of counterfeit protection and design is elementary. In some cases, highly decorative and innovative authentication solutions are used to protect consumers from tampering. These include authentication solutions that are both visible and invisible to the human eye. Holograms and iridescent materials also belong to the genre of authentication solutions. Furthermore, there are three different types of authentication solutions: visible (overt), invisible (covert) and forensic authentication solutions. A visible security label is, for example, a hologram. An invisible security label is e.g. a secret ink and a forensic security label is a marker system which requires complex detection devices (e.g. microscopes). According to the current state of the art, it is not possible to store information with this technology. This is a decisive disadvantage compared to track & trace solutions.

U.S. Pat. No. 9,382,432 B1, WO 2013/188927 A1 and U.S. Pat. No. 6,692,031 B1 describe invisible authentication solutions based on a type of secret ink containing different quantum dots with different fluorescence lifetimes. The different fluorescence durations change the fluorescence spectrum of the secret ink over time, giving it a temporal dimension.

Currently, both technologies are rarely combined to form a CPS. DE 10 2019 216 003.4 describes a method for marking products using an ink formulation containing semiconducting inorganic nanocrystals that emit radiation in the range of 750-1800 nm under photon excitation, in serialization and/or track & trace systems.

The present invention describes an innovative printable CPS model in which data is stored in a physical security feature of a multi-dimensional code that also includes a temporal dimension. Thus, the labeled products are more resistant to counterfeiting, because counterfeiters would have to print the continuing physical security feature and/or marker system on the product. The method according to the invention provides a secure identity that can find application as a CPS in Industry 4.0 and Logistics 4.0 or document security.

SUBJECT MATTER OF THE INVENTION

The present invention relates to a method of labeling products comprising the steps of:
- providing two or more ink formulations, each containing one or more photoluminescent dyes, preferably one photoluminescent dye, which emit radiation under photon excitation in the range of 380-3000 nm, preferably from 450 to 1800 nm, most preferably from 750 nm to 1100 nm, wherein the ink formulations differ by different photoluminescence lifetimes of the photoluminescent dyes;
- generating a multi-dimensional code for identifying a product, wherein at least one dimension, preferably two dimensions, is/are a spatial dimension and one dimension is a temporal dimension, based on the photoluminescence lifetimes of the photoluminescent dyes;
- printing the ink formulations on at least one area of the surface of the product in the form of said multi-dimensional code;
- irradiating the product printed with the ink formulation with photons;
- detecting the radiation emitted by the irradiated product in the range from 380 to 3000 nm, preferably from 450 to 1800 nm, most preferably from 750 nm to 1100 nm, as well as the time course of the photoluminescence lifetime over a period of time from 1 ns to 1 min, preferably 1 ns to 1 s, more preferably 1 ns to 1 ms, most preferably 5 ns to 100 µs after the start of the irradiation.

Also, the invention relates to an optical time-dependent security feature on at least one surface area of a product in the form of a multi-dimensional code comprising two or more photoluminescent dyes that emit radiation in the range of 380-3000 nm under photon excitation and differ in their photoluminescence lifetimes.

Further, the invention relates to the use of the optical time-dependent security feature as described herein as a cyber-physical system (CPS) for product monitoring.

Further, the invention relates to the use of the optical time-dependent security feature as described herein as a cyber-physical system (CPS) for document security.

In addition, the invention relates to a serialization and/or track & trace system that includes an optical time-dependent security feature that includes a multi-dimensional code printed on a product as described herein.

Furthermore, the invention relates to the use of a multi-dimensional code printed on a product as described herein as an optical, time-dependent security feature in a serialization and/or track & trace system.

Finally, the invention relates to the use of a multi-dimensional code printed on a product as described herein as an optical, time-dependent security feature for document security.

Definitions

The term "products" as used in the present invention includes the products themselves, to the extent that they are subject to marking, their packaging, product signs (tags), barcode cards and barcode labels, as well as any other means by which a product would normally be marked during the production process and/or transportation. Products include produce and its intermediate stages, commercial goods, and documents. Some examples are listed below: a branded product, a consumer product, a pharmaceutical product, a health product, a nutritional product, a component, a hardware component, an electronic component, a computer chip, a book, a manual.

The term "documents" as used in the present invention includes natural cellulose-based substrates, man-made polymer-based substrates, and mixtures thereof, including, but not limited to banknotes, identification cards, passports, birth certificates, tickets, admission tickets, and other tickets. Some other examples are listed below: a check, a bond, a bank card, a credit card, a check card, a currency, a money card, an identification item, an identity item, an access item, a permit item, an identification card, a driver's license, a personalized item, a passport, a document, a paper document, a security document, a stamp, a personalized document, a certificate, a stock certificate, a debt certificate, a contract, an insurance policy, a will, a parking ticket, a transportation ticket, or a ticket for admission to an event.

The term "ink formulation" in the sense of the present invention includes any solvent and combinations thereof as well as typical additives suitable for the production of a printable liquid.

Photoluminescence refers to the emission of photons after prior excitation by means of photons of higher energy, usually in the ultraviolet, but also visible range. The excitation promotes an electron to a higher energy state. When it falls back to a lower energy state, this energy is released again in the form of photons. In a luminescent substance, a rough distinction is made between two types of excitation: in fluorescence, the electron falls back from a higher singlet state to the lower energy state, while in phosphorescence, the excited electron passes to an elevated triplet state through a transition forbidden by spin selection, from which it in turn falls back to the lower energy state through a transition forbidden by spin selection.

Under the term of photoluminescence lifetime the fluorescence lifetime as well as the phosphorescence lifetime is divided.

The term "fluorescence lifetime" as used in the present invention indicates the average time that a molecule remains in an excited singlet state during fluorescence before it emits a photon and thus returns to the lower energy state.

The term "phosphorescence lifetime" as used in the present invention indicates the average time a molecule remains in an excited triplet state during phosphorescence before emitting a photon and thus returning to the ground state.

The term "multidimensional code" in the sense of the present invention includes at least a spatial dimension (i.e. in the x-direction), a color dimension of the photoluminescence of the photoluminescent dyes and a temporal dimension based on the measurement of the photoluminescence lifetimes of the photoluminescent dyes used. Other possible dimensions include another spatial dimension (i.e., in the y-direction) and a color dimension, via the inherent color of the dyes on a substrate as a multicolor code.

The term "printing" as used in the present invention includes the deposition of pigments onto or into a solid substrate. Typical examples include, but are not limited to, digital printing, inkjet printing, screen printing, transfer printing, stamp printing, roll to roll, non-contact printing, laser printing, and other processes.

The term "irradiation" as used in the present invention includes excitation of the photoluminescence emission signal and photoluminescence lifetime. Various excitation sources may serve for the emission signal. Some examples include: LEDs, helium/xenon lamps, laser diodes.

For the photoluminescence lifetime, usually the pulse of the excitation will be shorter in time than the photoluminescence lifetime of the pigments. Laser diodes are readily taken for this purpose.

The term "detection" in the sense of the present invention includes, on the one hand, the detection of the emission signal of the photoluminescent pigments. Detectors made of silicon and germanium are suitable for this purpose. On the other hand, it also comprises the spatial and temporal detection of the photoluminescent decay times of the respective pigments. This requires special sensors and detectors that can resolve a temporal sequence.

FIGURES

Figure 3:
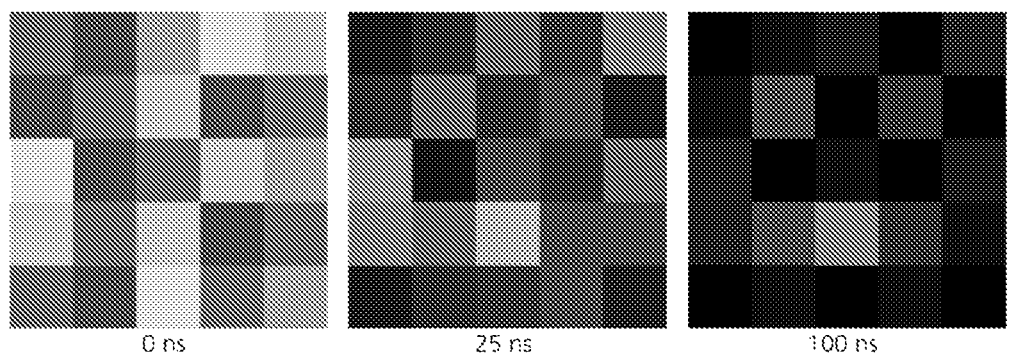

FIG. 3 shows a simulated example of a four-dimensional code with two spatial dimensions in x- and y-direction, a color dimension by the photoluminescence of the photoluminescent dyes, represented by different colors, as well as a temporal dimension by the different fluorescence lifetimes as detected images in a time period of 0 ns (left), 25 ns (center) and 100 ns (right) after the beginning of the irradiation with photons.

DETAILED DESCRIPTION OF THE INVENTION

The present invention relates to a method of labeling products comprising the steps of:
  Providing two or more ink formulations, each containing one or more photoluminescent dyes, preferably one photoluminescent dye, that emit radiation under photon excitation in the range of 380-3000 nm, preferably from 450 to 1800 nm, most preferably from 750 nm to 1100 nm, wherein the ink formulations differ by different photoluminescence lifetimes of the photoluminescent dyes;
  generating a multi-dimensional code for identifying a product, wherein at least one dimension, preferably two dimensions, is/are a spatial dimension and one dimension is a temporal dimension, based on the photoluminescence lifetimes of the photoluminescent dyes;
  printing the ink formulations on at least one area of the surface of the product in the form of said multi-dimensional code;
  irradiating the product printed with the ink formulation with photons;
  detecting the radiation emitted by the irradiated product in the range from 380 to 3000 nm, preferably from 450 to 1800 nm, most preferably from 750 nm to 1100 nm, as well as the time course of the photoluminescence lifetime over a period of time from 1 ns to 1 min, preferably 1 ns to 1 s, more preferably 1 ns to 1 ms, most preferably 5 ns to 100 us after the start of the irradiation.

Two or more ink formulations are initially provided, each containing one or more photoluminescent dyes, preferably one photoluminescent dye, which emit radiation in the range of 380-3000 nm under photon excitation and have a photoluminescence lifetime of 1 ns-1 min.

The number of ink formulations is generally not limited and is subject only to practical, economic and safety considerations. In general, the greater the number of ink formulations, the higher the complexity and thus the information content of the unique multidimensional code to be printed. The number of ink formulations is certainly limited upwards by the maximum number of ink formulations that can be processed by the printer used and by price restrictions. Typically, between 2 and 30 ink formulations are used in the method according to the invention, preferably 2 to 25 ink formulations, more preferably 2 to 20 ink formulations, most preferably 3 to 15 ink formulations.

The ink formulations are preferably commercially available ink formulations suitable for depositing pigments onto or into a solid substrate. Typical examples include, but are not limited to, digital printing, inkjet printing, screen printing, transfer printing, stamp printing, roll-to-roll, non-contact printing, laser printing, and other processes. One or more photoluminescent dyes may then be added to these commercially available ink formulations.

In another embodiment, the ink formulations contain no color pigments other than the photoluminescent dyes. In this embodiment, the multidimensional code printed with the ink formulations is not visible to the human eye because of the concentration of the photoluminescent dyes. Thus, the multidimensional code is not immediately apparent but can be detected and read only after irradiation of the product printed with the ink formulations with photons via detection of the radiation emitted by the irradiated product in the range of 380-3000 nm.

In a next embodiment, the ink formulations do not contain any color pigments other than the photoluminescent dyes. In this embodiment, the multidimensional code printed with the ink formulations is visible to the human eye due to the high concentration of the ink formulations (inherent color of the photoluminescent dyes). The multidimensional code is therefore immediately visible. After irradiating the product printed with the ink formulations with photons, the emitted radiation in the range of 380-3000 nm can be detected and read.

In a fourth embodiment, a multidimensional code is first printed on at least one surface of the product using a commercially available ink formulation. Then, in a second step, the ink formulations containing the photoluminescent dyes are spot printed on the existing multidimensional code in the form of drops and/or other patterns, such as areas, stripes, lines, geometric figures, such as circles, triangles, rectangles, polygons, etc., alphanumeric characters, or combinations thereof. In this embodiment, the ink formulations preferably do not contain pigments other than the photoluminescent dyes, so that the droplets and/or the further multidimensional code are not visible to the human eye.

In a fifth embodiment, a multidimensional code is first printed on at least one surface of the product using a commercially available ink formulation. Then, in a second step, the ink formulations containing the photoluminescent dyes are spot-applied in the form of additional multidimensional codes. In this embodiment, the ink formulations preferably contain no pigments other than the photoluminescent dyes, so that the droplets and/or the further multidimensional code are not visible to the human eye.

In a sixth embodiment, according to one of the preceding embodiments, an additional unique code is generated during the printing process—due to, for example, the high printing frequency and deflections of the ink drops.

In a seventh embodiment, according to one of the preceding embodiments, the multi-dimensional code is printed on at least one label that is subsequently adhered to at least one surface of the product.

In an eighth embodiment, the unique multi-dimensional code according to one of the preceding embodiments is printed on product signs (tags), barcode cards, and/or barcode labels.

In a ninth embodiment, the unique multi-dimensional code is printed on documents according to one of the preceding embodiments.

Each ink formulation contains one or more, such as 2, 3, 4, 5 or more photoluminescent dyes. Preferably, each ink formulation contains one photoluminescent dye.

The photoluminescence lifetimes of the photoluminescent dyes used are typically in the range of 1 ns to 1 min, preferably in the range of 1 ns to 1 s, more preferably in the range of 1 ns to 1 ms, most preferably in the range of 5 ns to 100 µs.

The photoluminescence lifetimes of the various photoluminescent dyes used in the ink formulations typically differ in the range of 1 ns to 1 min, preferably in the range of 1 ns to 1 s, more preferably in the range of 1 ns to 1 ms, most preferably in the range of 5 ns to 100 µs.

The photoluminescence lifetimes of the photoluminescent dyes can be identified, for example, in decay diagrams of emission spectra.

The photoluminescent dyes can be selected from fluorescent dyes, phosphorescent dyes and mixtures thereof.

Fluorescent dyes are dyes that emit fluorescent radiation after photon excitation, while phosphorescent dyes are dyes that emit phosphorescent radiation after photon excitation.

The selection of phosphorescent dyes is generally limited only in that under photon excitation emit radiation in the range of 380-3000 nm, preferably from 450 to 1800 nm, most preferably from 750 nm to 1100 nm.

The phosphorescent dyes used in this patent can exhibit both a "stoke shift" and an "anti-stoke shift" under photon excitation. Furthermore, luminous materials can exhibit both fluorescence, and phosphorescence behavior. The luminous materials used can be organic as well as inorganic crystals/molecules.

Fluorescent dyes are typically selected from organic fluorescent dyes and inorganic fluorescent dyes or mixtures thereof.

Organic dyes can be selected from the classes of proteins and peptides, small organic molecules, synthetic oligomers and polymers, and multicomponent systems.

Typical examples of polymers and peptides are Green Fluorescent Protein (GFP), Yellow Fluorescent Protein (YFP) or Red Fluorescent Protein (RFP).

Non-proteinic organic fluorescent dyes usually belong to the classes of xanthene derivatives, cyanine derivatives, squarain derivatives, squarain rotaxane derivatives, naphthalene derivatives, coumarin derivatives, oxadiazole derivatives, anthracene derivatives, pyrene derivatives, oxazine derivatives, acridine derivatives, arylmethine derivatives, tetrapyrrole derivatives and dipyrromethane derivatives. Organic fluorescent dyes are usually commercially available in all emission spectral colors from blue (from 380 nm) to red (up to 3000 nm).

Suitable organic dyes with emission spectral colors from 800 nm are described, for example, in EP 0 933 407, U.S. Pat. Nos. 5,282,894, 5,665,151, WO 1998/018871, WO 2003/038003, U.S. Pat. Nos. 10,119,071 and 5,542,971.

Suitable inorganic dyes are preferably semiconducting inorganic nanocrystals.

The semiconducting inorganic nanocrystals are preferably selected from the group consisting of perovskites, I-VI semiconductors, II-VI semiconductors, III-V semiconductors, IV-VI semiconductors, semiconductors, carbon dots, and mixtures thereof.

Examples of suitable semiconducting inorganic nanocrystals include AgS, AgSe, AgTe, CdS, CdSe, CdTe, PbS, PbSe, PbTe, SnTe, ZnS, ZnSe, ZnTe, InP, InAs, $Cu_2S$, $In_2S_3$, InSb, GaP, GaAs, GaN, InN, InGaN, ZnSSe, ZnSeTe, ZnSTe, CdSSe, CdSeTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, CdSeCdS, $CuInS_2$, $CuInSe_2$, $CuInGaSe_2$, $CuInZnS_2$, $CuZnSnSe_2$, $CuTn(S,Se)_2$, $CuInZn(S,Se)_2$, $AgIn(S,Se)_2$.

Other suitable examples, but not limited to, are perovskite materials having the general formula $ABX_3$ or $A_4BX_6$, wherein X may be selected from Cl, Br, I, O and/or mixtures thereof, wherein A may be selected from Cs, $CH_3NH_3$, $CH(NH_2)_2$, Ca, Sr, Bi, La, Ba, Mg and/or mixtures thereof, wherein B may be selected from Pb, Sn, Sr, Ge, Mg, Ca, Bi, Ti, Mn, Fe and/or mixtures thereof.

Furthermore, core/shell and/or core/multishells of semiconducting inorganic nanocrystal architectures of II-VI, III-V, IV-VI, I-VI, semiconductors or mixtures thereof, and core/shell and/or core/multishells of perovskite materials, are other suitable examples.

The crystal lattice of the semiconducting inorganic nanocrystals may additionally, but not exclusively, be doped with one or more metal ions, such as $Cu^+$, $Mg^{2+}$, $Co^{2+}$, $Ni^{2+}$, $Fe^{2+}$, $Mn^{2+}$ and/or with one or more rare earth metals, such as ytterbium, praeseodymium or neodymium.

The semiconducting inorganic nanocrystals preferably have an average particle size from 1 nm to 100 nm, more preferably from 2 nm to 50 nm, and most preferably from 3 nm to 15 nm in at least one dimension, preferably in all dimensions. The average particle size can be further increased/modified by various methods. Typical examples include, but are not limited to, a silica shell, a titanium oxide shell, a halogen shell, and other methods for stability enhancement, masking, biocompatibility, water solubility, and/or coating.

A property of semiconducting inorganic nanocrystals of interest to the present invention is that their excitation and emission spectra depend, among other things, on their particle size.

Furthermore, "anti-stoke-shift" materials can also be used in the sense of the inventions. These phosphors are usually doped with the elements scandium and yttrium as well as the elements of the lanthanide or actinide group. The chemical composition of these phosphors is composed of the host lattice, the donor ions and the acceptor ions. The chemical composition affects their spectral properties.

In the spirit of the invention, phosphorescent materials can also be used. Phosphorescent materials are usually crystals which are contaminated with a dopend. Phosphorescent dyes are usually selected from doped oxides, nitrides, oxynitrides, sulfides, selenides, halides, silicates and aluminates of calcium, strontium, barium, zinc, cadmium, manganese, silicon and rare earth metals and mixtures thereof. Mostly, but not exclusively, sulfides of metals of the second main group of the periodic table and zinc and aluminates of metals of the second main group of the periodic table are used. The dopends can represent, for example, metals or metal salts. Suitable examples of phosphorescent dyes are doped sulfides and aluminates of calcium, strontium, barium and zinc, such as calcium/strontium sulfide doped with bismuth, zinc sulfide doped with copper, and strontium aluminate doped with europium.

The photoluminescent dyes with a "stoke-shift" behavior used in the method according to the invention are preferably photoluminescent substances which are brought into electronically excited energy states by light absorption of a higher-energy photon, and thereupon again reach lower-energy states by emitting light in the form of fluorescence or phosphorescence.

The photoluminescent dyes with an "anti-stoke-shift" behavior used in the method according to the invention are preferably photoluminescent substances that emit a light quantum with higher energy by light absorption of two low-energy photons. Usually, there are two processes to generate an "anti-stoke-shift" behavior. On the one hand, the pigments are irradiated by a high photon flux (usually laser) so that two low-energy photons can emit a higher-energy light quantum.

On the other side, the pigments are irradiated by photon flux so that a metastable supernatant state is generated. By absorbing a photon again, a light quantum of higher energy can now be emitted.

The photoluminescent dyes with "stoke-shift" behavior are preferentially excited by UV light, visible light such as blue or white light, and higher energy near-infrared radiation than the emission signal.

The photoluminescent dyes with "anti-stoke-shift" behavior are preferentially excited by near-infrared (NIR) radiation, especially radiation of wavelengths between 750-1600 nm.

Under photon excitation, the photoluminescent dyes emit radiation with a wavelength in the range from 380 to 3000 nm, more preferably from 450 to 1800 nm, most preferably from 750 nm to 1100 nm.

The proportion of the photoluminescent dyes in the ink formulation is, independently of one another, in each case preferably from 0.01 to 70.0% by weight, more preferably from 0.05 to 40.0% by weight, most preferably from 0.09 to 30.0% by weight, of the total weight of the ink formulation. For digital and inkjet printing, a range between 0.01-30.0 wt % is preferred.

The ink formulations may contain photoluminescent dyes that share at least one or more, preferably all, of the following properties: Emission wavelength, Emission distribution, Emission maximum.

In another embodiment, the ink formulations may contain mixtures of photoluminescent dyes that have different values of emission wavelength, emission distribution, and emission maximum.

Furthermore, the ink formulations can contain the color pigments of the commercial inks. Commercial ink formulations can be used and the photoluminescent dyes can be added to them.

The emitted radiation from the ink formulations can result in an individual photoluminescence spectrum that is dependent on the type, amount, particle size, inherent color, and especially the photoluminescence lifetime of the photoluminescent dyes.

In this case, the individual photoluminescence spectrum can be detected with a spectrometer. The detected individual photoluminescence spectrum can then be compared with a reference spectrum stored in a database. The individual photoluminescence spectrum contains a temporal component due to the use of photoluminescent dyes with different photoluminescence lifetimes, which causes the individual photoluminescence spectrum to change over time, preferably a period of 1 ns to 1 min, preferably 1 ns to 1 s, more preferably 1 ns to 1 ms, most preferably 5 ns to 100 µs after the start of irradiation. These changes can be mapped and compared using various methods. First, measurements of the respective photoluminescence spectrum can be made over a period of 1 ns to 1 min, preferably 1 ns to 1 s, more preferably 1 ns to 1 ms, most preferably 5 ns to 100 µs after the start of the irradiation at fixed times, which are then compared with corresponding reference spectra from the same times stored in a database. Alternatively, a "film" of the individual fluorescence spectrum can be recorded over a period of 10 ns to 1 s, preferably 20 ns to 100 ms, more preferably 50 ns to 10 ms, most preferably 75 ns to 1 ms after the start of the irradiation and compared with a reference film stored in a database.

This individual time-dependent fluorescence spectrum can be used as a further security feature for a number of different ink formulations individually assembled by the producer of the product.

The ink formulations each preferably have a reciprocal Ohnesorg number of less than 14, more preferably from 1 to 10, even more preferably from 1 to 8, and most preferably from 2 to 4.

In a further step, a multidimensional code for identifying a product is generated, wherein at least one dimension, preferably two dimensions, is/are a spatial dimension and one dimension is a temporal dimension, based on the photoluminescence lifetimes of the photoluminescent dyes.

Suitable dimensions for the multidimensional code are spatial dimensions, for example in x- and/or y-direction, color dimensions, for example the intrinsic color of the dyes on a substrate as multicolor code and/or the photoluminescence of the photoluminescent dyes emitted into space and onto the substrate, as well as the temporal dimension over the photoluminescence lifetimes of the photoluminescent dyes.

The multidimensional code can be a three-dimensional, four-dimensional, five-dimensional.

Example of a three-dimensional code is
a bar code containing photoluminescent dyes, where the photoluminescent dyes also have different photoluminescence lifetimes (1 spatial dimension, 1 color dimension, 1 temporal dimension).

Examples of a four-dimensional code are:
a multicolor bar code containing photoluminescent dyes, where the photoluminescent dyes also have different photoluminescence lifetimes (1 spatial dimension, 2 color dimensions, 1 temporal dimension);
a QR code containing photoluminescent dyes, wherein the photoluminescent dyes also have different photoluminescence lifetimes (2 spatial dimensions, 1 color dimension, 1 temporal dimension);

Example of a five-dimensional code is:
a multicolor QR code containing photoluminescent dyes, wherein the photoluminescent dyes also have different photoluminescence lifetimes (2 spatial dimensions, 2 color dimensions, 1 temporal dimension).

The multidimensional code may also include one or more patterns, such as areas, stripes, lines, geometric figures, such as circles, triangles, rectangles, polygons, etc, alphanumeric characters, or combinations thereof.

The multidimensional code may also be a unique multidimensional code.

For this purpose, preferably at least one reference quantity, preferably several reference quantities of the product can first be encoded with the aid of a unique key. Possible reference variables here are, for example, reference variables relating to the type and nature of the product, such as serial numbers, lot numbers, CAS numbers in the case of chemical products, the production location, the production time, the delivery location, the producer, the supplier, the customer or similar.

The unique key can be an algorithm provided to the producer or created by the producer.

A code unique to the product, preferably to the individual package unit of the product, is generated via the encryption.

The ink formulations are printed on at least one area of the surface of the product in the form of the multidimensional code.

Upon generation of a unique multidimensional code, each packaging unit of the product is preferably printed with its own unique multidimensional code.

In a special embodiment, an additional unique multidimensional code is generated during the printing process by an individual print pattern—caused by imperfections in the individual print pattern, e.g. due to the high printing frequency and deflections of the ink drops. In this case, an actually unique code is generated by each printing process, since the imperfections in the individual print pattern cannot be reproduced.

The step of "printing the ink formulations on at least one area of the surface of the product in the form of this multidimensional code" comprises here both the printing of the ink formulations directly on at least one area of the surface of the product, insofar as the concreteness of the product permits this, and also the printing of the ink formulations on at least one label in the form of this multidimensional code and pasting/labeling of the surface of the product with at least one printed label.

If the shape and/or concreteness of the product does not permit direct labeling, the step of "printing the ink formulations on at least one area of the surface of the product in the form of this multidimensional code" may also comprise printing the ink formulations directly on at least one area of the surface of the packaging of the product or pasting/labeling the surface of the product with at least one printed label. The multidimensional code may also be printed on documents.

For this purpose, the usual printing methods are applicable depending on the type of ink formulations. Preferably, the ink formulations are printed on at least one surface of the surface of the product or document using digital printing, screen printing, transfer printing, roll to roll printing methods, "no contact" printing methods, or laser printing.

Depending on the type of product, the multidimensional code can be printed directly on the surface of the product or document, on the packaging of the product, and on labels, signs, barcode cards, and/or barcode labels.

In addition to the multidimensional code, the ink formulations may also be printed in other patterns and unique codes, such as areas, stripes, lines, geometric figures, such as circles, triangles, rectangles, polygons, etc., alphanumeric characters, or combinations thereof, on at least one surface of the surface of the product. The printed pattern may serve here as a pure time-dependent authentication feature or may contain information, such as safety and usage instructions or manufacturer information.

Preferably, the ink formulations are printed side by side to form a layer of dots of different photoluminescent dye compositions that provide a time-dependent pattern of the multi-dimensional code.

In some embodiments, the ink formulations are printed side-by-side and optionally on top of each other to form one and/or more layers of dots of different photoluminescent dye compositions that provide a time-dependent pattern of the multi-dimensional code.

In a further step, the product printed with the ink formulations is irradiated with photons.

The photon irradiation causes the photoluminescent dyes in the ink formulations to enter excited energy states (excitation).

Preferably, the product printed with the ink formulations is irradiated with ultraviolet visible light, such as blue or white light, or NIR light, preferably ultraviolet blue or white light.

For example, a black light lamp, halogen lamp, or LED lamp, preferably a blue or white LED lamp, serves as the light source. In addition, a suitable light source for irradiation is an LED flash, such as the LED flash of a terminal device, such as a smartphone or tablet.

After irradiation, the irradiated product, preferably photoluminescent dyes in the ink formulations, emits radiation in the range from 380 to 3000 nm, preferably from 450 to 1800 nm, most preferably from 750 nm to 1100 nm. This is detected in a further step over a period of 1 ns to 1 min, preferably 1 ns to 1 s, more preferably 1 ns to 1 ms, most preferably 5 ns to 100 µs after the start of irradiation.

Usually, the irradiation time is shorter than the photoluminescence lifetime of the photoluminescent dyes.

The irradiation can be either pulsed photon irradiation or continuous photon irradiation.

Pulsed photon irradiation is usually performed when using photoluminescent dyes with short photoluminescence lifetimes up to a few ms, preferably when using fluorescent dyes.

Continuous photon irradiation is usually performed when using photoluminescent dyes with longer photoluminescence lifetimes starting from a few ms, preferably when using phosphorescent dyes.

The emitted radiation can be detected with any detection device suitable for this purpose.

In the temporal dimension, the individual photoluminescence spectrum of the multidimensional code is observed over a period of 1 ns to 1 min, preferably 1 ns to 1 s, more preferably 1 ns to 1 ms, most preferably 5 ns to 100 µs after the start of irradiation, and changes over this period are noted. These changes are due to the different photoluminescence lifetimes of the photoluminescent dyes used, which ensure that emitted radiation from one photoluminescent dye decays earlier than that from another, resulting in a change in the pattern of the multidimensional code over time.

These changes can be noted and matched on a point-by-point basis, for example by recording two or more spectra of the emitted radiation at fixed times during the detection period.

In addition to or instead of spectra, images of the emitted radiation can also be taken at the respective fixed times and then the changes in these images can be matched. Alternatively, these changes can be noted continuously, for example by making a movie of the emitted radiation during the detection period.

Various parameters of the pattern of the multidimensional code and their changes can be noted, such as changes in the pattern in the x and y directions, color, photoluminescence, or their lifetime.

These parameters can then be stored in and retrieved from at least one database. The measured parameters can then be matched with the parameters stored in the database. The pattern of the multidimensional code can thus be used as an optical time-dependent authentication feature.

The method according to the invention may thus comprise the following further steps:
- storing the multidimensional code in at least one database;
- retrieving the multidimensional code from the database; and
- matching this code with the detected code to verify or authenticate the product.

The method can further be used in serialization and/or track & trace systems.

In serialization, structured data is mapped to a sequential representation form. Serialization is mainly used for transferring objects over the network in distributed software systems.

For use in serialization systems, the following additional steps are preferred:
- storing the unique multidimensional code in at least one database;
- retrieving the unique multidimensional code from the database; and
- matching this code with the detected code to verify the product.

In more advanced serialization systems, one or more reference quantities of a product can be recorded and/or encoded using a unique key. A unique multi-dimensional code is generated via a corresponding serialization and/or track & trace computer program, which is printed on the product. Additionally, the code is stored in a database, preferably a central database. The code can then be scanned and read from the database at any time. The serialization and/or track & trace computer program can thus be used to read out the coded reference quantities of the product.

For use in track & trace systems, it is further preferred that the ink formulation is additionally printed on at least one area of the surface of a packaging group containing the product, for example selected from bundles, outer packaging, pallets, in the form of the unique code.

This enables complete tracking of the product during the production and transportation path of the individual product.

The present method thus represents a combination of track & trace technology and optical security features. Thus, the traceability process and the authentication process of products are united.

Furthermore, the method can be used to secure documents such as banknotes, ID cards, passports, birth certificates, tickets, admission tickets and other tickets, or other documents as described herein.

Figure 1:
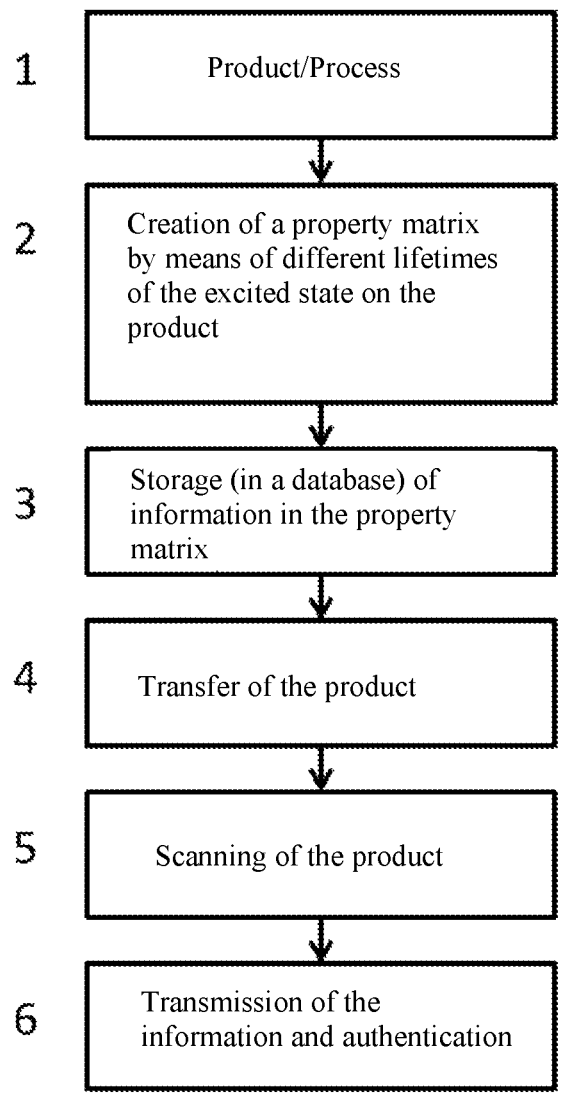
FIG. 1 shows an overview of a possible embodiment of the method for marking products according to the invention.

FIG. 1 shows an overview of a possible embodiment of the method according to the invention in a track & trace system.

Here, in a first step, reference variables of a product, such as production location and period, ingredients of the product, dosage forms, etc., are identified.

These reference variables are then linked in a property matrix using the different fluorescence lifetimes of the various fluorescent dyes to create a multidimensional code unique to the product. This code can be a two-dimensional, three-dimensional or four-dimensional code, e.g. a bar code, a QR code or a colored bar code, each with a temporal dimension linked to the different fluorescence lifetimes of the different fluorescent dyes. The code is printed on the surface of the product using the ink formulations disclosed herein with the fluorescent dyes used for the property matrix. Depending on the product, the code may be printed directly on the surface of the product or on the packaging of the product.

Information from the properties matrix is stored in a central database, for example via a track & trace computer program.

The product can now be passed on, for example to a new production stage or to sales. In the new environment, the product is now scanned for identification and the code is read.

The code printed using the ink formulations revealed therein can now be used as a Track & Trace identifier.

The code is transferred to the Track & Trace computer program. In the process, the code is read from the database. In this way, the reference quantities of the marked product are preserved.

The code as well as all other possible markings with the ink formulations disclosed herein can also be used as an optical authentication marking (as shown in FIG. 1). For this purpose, the surface of the product is exposed to light, preferably white or blue light. The photoluminescent substance, preferably the fluorescent dyes in the ink formulations, are thereby excited as discussed above and then emit photoluminescent radiation in the range of 400-1800 nm (visible and NIR radiation). This radiation can only partially (up to about 800 nm) not be perceived by the human eye. Instead, an electronic device that can detect the visible and NIR photoluminescence radiation is required for detection. Spectrometers or NIR cameras would be suitable, for example.

The excitation and detection can be controlled so that, after excitation and detection, a number of measurements taken at fixed times over a period of 1 ns to 1 min, preferably 1 ns to 1 s, more preferably 1 ns to 1 ms, most preferably 5 ns to 100 μs after the start of the irradiation, or a movie of the code taken over this period, appears on the screen of the terminal device. This photo thus serves as an optical time-dependent authentication feature and allows the time-dependent authentication of the product.

When used in a serialization or track & trace system, the method according to the invention thus extends this system by a time-dependent optical security feature that is partially invisible to the human eye (750-3000 nm).

The method according to the invention increases security through the time dimension, because an individual time-dependent photoluminescence spectrum is emitted in the visible and NIR range, which can be detected with the help of a spectrometer. In addition, the method according to the invention increases the complexity and the storage volume of the code due to the additional usable dimensions of the time-dependent pattern. This individual time-dependent photoluminescence spectrum can in turn be used as an additional authentication feature. Through this time-dependent authentication feature, the security feature, e.g. a QR code with time-dependent second factor, can be used as a CPS of the Secure Identity in Industry 4.0 and Logistics 4.0 (supply chain security) level. Compared to other authentication features such as RFID chips or holograms, the method according to the invention also has a clear cost advantage.

The present invention also relates to an optical time-dependent security feature on at least one area of the surface of a product in the form of a multidimensional code containing two or more fluorescent dyes that emit radiation in the range of 380-3000 nm under photon excitation and are distinguished by different fluorescence lifetimes.

Furthermore, the invention relates to an optical, time-dependent security feature on at least one area of the surface of a product in the form of a multidimensional code that contains photoluminescent dyes that emit radiation in the range of 380-3000 nm under photon excitation and differ in their photoluminescence lifetimes.

The optical, time-dependent security feature is thereby preferably printed on at least one area of the surface of the product using the method according to the invention.

Further, the invention relates to the use of the optical time-dependent security feature as described herein as a cyber-physical system (CPS) for product monitoring.

Furthermore, the invention relates to the use of the optical time-dependent security feature as described herein as a cyber-physical system (CPS) for document security.

The present invention further relates to a serialization and/or track & trace system comprising an optical time-dependent security feature comprising a multi-dimensional code printed on a product as described herein.

Additionally, the invention relates to the use of a multi-dimensional code printed on a product as described herein as an optical, time-dependent security feature in a serialization and/or track & trace system.

Additionally, the invention relates to the use of a multi-dimensional code printed on a product as described herein as an optical, time-dependent security feature for document security.

In this regard, the method according to the invention increases security through the time dimension because an individual time-dependent photoluminescence spectrum is emitted in the visible and NIR range, which can be detected using a spectrometer. In addition, the method according to the invention increases the complexity and the storage volume of the code due to the additional usable dimensions of the time-dependent pattern.

In this regard, the unique multidimensional code is printed on the product or product packaging or a document using the ink formulations described herein, which include photoluminescent dyes that emit radiation in the range of 380-3000 nm when excited by photons and are distinguished by different photoluminescence lifetimes.

The features of the code, ink formulations, and photoluminescent dyes described herein are also applicable to the optical time-dependent security feature, serialization and/or track & trace system, and uses according to the invention.

Likewise, the features of the serialization and/or track & trace system described herein are applicable.

Figure 2:
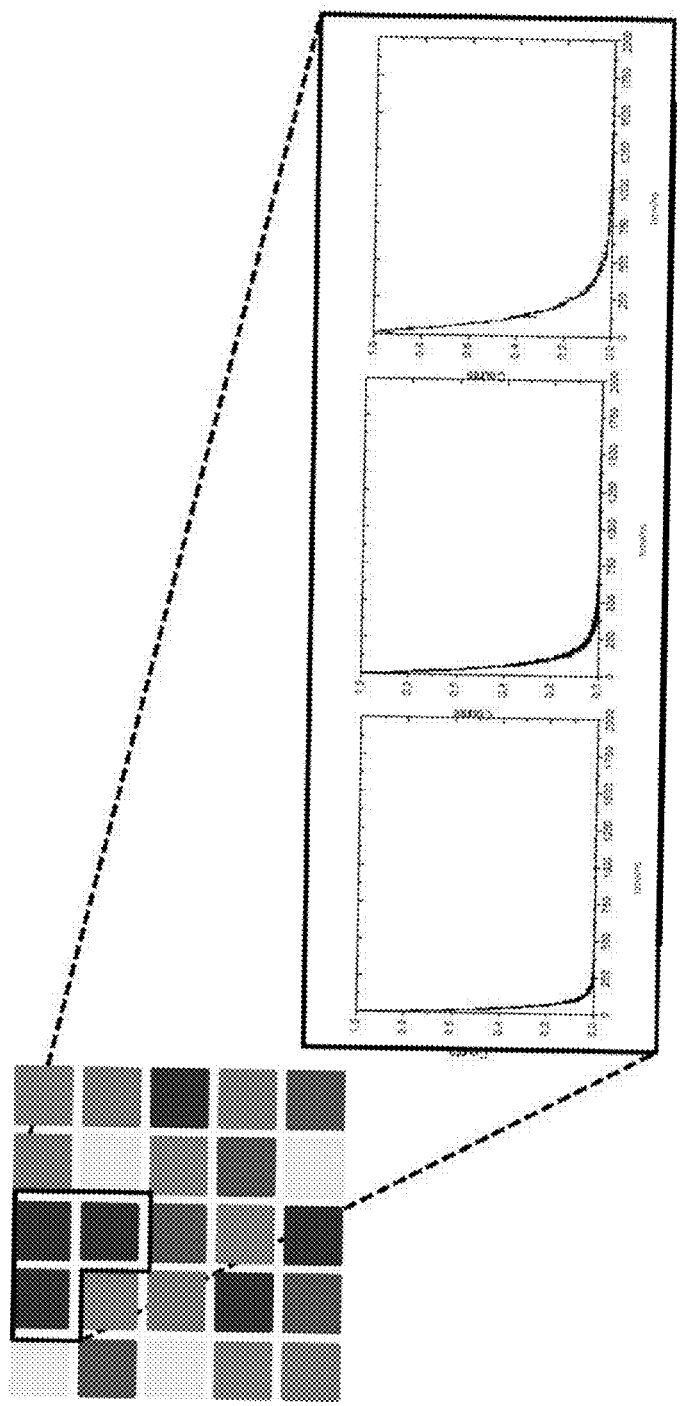
FIG. 2 shows an example of a four-dimensional code with two spatial dimensions in x- and y-direction, a color dimension by the fluorescence of the fluorescent dyes, represented by different colors, as well as a temporal dimension by the different fluorescence lifetimes of the three "red" fluorescent dyes after pulsed excitation. The decay times are shown as counts over time in ns.

FIG. 2 shows an example of a printed four-dimensional code. The code consists of a square of 5×5 squares printed side by side of different ink formulations. The five different shades of gray in the printed squares indicate ink formulations with five different fluorence colors. In highlighted different squares with one fluorescent color, indicated in dark gray, ink formulations with different fluorescent dyes were also used, which have different fluorescence lifetimes. These are shown in the decay diagrams as counts over time in ns.

In the decay spectrum on the left, semiconducting nanoparticles of CdSeCdS with an emission maximum at 621 nm and a fluorescence lifetime of 40 ns were used.

In the middle decay spectrum, semiconducting nanoparticles of CdSeCdS with an emission maximum at 623 nm and a fluorescence lifetime of 89 ns were used.

In the right decay spectrum, semiconducting nanoparticles of CdSeCdS with an emission maximum at 625 nm and a fluorescence lifetime of 157 ns were used.

The code thus includes two spatial dimensions in the x and y directions, a color dimension over five different fluorescence colors of the fluorescent dyes, and a temporal dimension over the different fluorescence lifetimes of the fluorescent dyes.

FIG. 3 shows an example of a temporal variation of a four-dimensional code. Again, the code consists of a square of 5×5 squares printed side by side from different ink formulations. The five different colors of the printed squares indicate ink formulations with five different fluorescent colors. The temporal dimension is revealed from images taken at different times after the start of irradiation. Immediately after the start of irradiation (0 ns), all 25 printed squares can be seen in color (left).

25 ns after the start of irradiation, different squares show different decay behavior. While some squares emit an almost unchanged fluorescence, other squares show a perceptible attenuation and the fluorescence of five squares is already extinguished in the measurable range, which is symbolized by a black square (center). The different decay behavior of the fluorescence radiation indicates different fluorescence lifetimes of the fluorescent dyes, with the black squares indicating very short fluorescence lifetimes, the attenuated squares indicating medium fluorescence lifetimes, and the unaltered squares indicating longer fluorescence lifetimes of the fluorescent dyes.

100 ns after the start of irradiation, only the five squares of fluorescent dyes with the longest fluorescence lifetimes emit fluorescence. These stylize a smiley. Thus, another simple authentication feature can be introduced via the temporal dimension of the code by arranging the fluorescent dyes with the different fluorescence lifetimes in the code in such a way that, depending on the decay time, different images and symbols become visible that can be used as authentication features.

The invention claimed is:

1. A method of labeling products comprising:
providing two or more ink formulations, each containing one or more photoluminescent dyes, that emit radiation in the range of 380-3000 nm under photon excitation, wherein the ink formulations differ by different photoluminescence lifetimes of the photoluminescent dyes;
generating a multi-dimensional code for identifying a product, wherein at least one dimension is a spatial dimension and one dimension is a temporal dimension, based on the photoluminescence lifetimes of the photoluminescent dyes;
printing the ink formulations on at least one area of the surface of the product in the form of said multi-dimensional code;
irradiating the product printed with the ink formulation with photons;
detecting the radiation emitted by the irradiated product in the range from 380 to 3000 nm, as well as the time course of this radiation over a period of time from 1 ns to 1 min.

2. The method according to claim 1, wherein the multi-dimensional code is a three-dimensional, four-dimensional or five-dimensional code.

3. The method according to claim 1, wherein the multi-dimensional code includes as a further dimension a color coding over the emission spectra of the photoluminescent dyes and/or a color coding over the absorption color of the dyes.

4. The method according to claim 1, wherein the ink formulations are printed separately side by side and optionally on top of each other on the surface of the product to generate the multidimensional code.

5. The method according to claim 1, wherein the photoluminescence lifetimes of the photoluminescent dyes in the ink formulations differ in the range from 1 ns to 1 min.

6. The method according to claim 1, wherein the multidimensional code comprises one or more patterns, wherein the one or more pattern comprises areas, stripes, lines, geometric figures, alphanumeric characters, or combinations thereof, wherein the geometric figures comprise circles, triangles, rectangles, polygons, or a combination thereof.

7. The method according to claim 1, further comprising:
storing the multidimensional code in at least one database;
querying the multidimensional code from the database; and
matching the code with the detected code to verify or authenticate the product.

8. The method according to claim 1, wherein the ink formulation is additionally printed on at least one area of the surface of a packaging group containing the product, wherein the packaging group comprises bundles, outer packaging, or pallets, in the form of the multidimensional code.

9. The method according to claim 1, wherein the ink formulation is printed on product signs (tags), barcode cards and barcode labels in the form of the multidimensional code.

10. The method according to claim 1, wherein the multidimensional code is a unique multidimensional code, wherein the unique multidimensional code generates at least one reference quantity of the product is encrypted using a unique key.

11. The method according to claim 1, wherein the ink formulation is printed on at least one area of the surface of the product using digital printing.

12. The method according to claim 1, wherein the product printed with the ink formulations is irradiated with ultraviolet, visible or NIR light for excitation.

13. The method according to claim 1, wherein two or more images and/or spectra of the emitted radiation are measured at predetermined times during the detection period.

14. The method according to claim 1, wherein the photoluminescent dyes comprise fluorescent dyes, phosphorescent dyes or a combination thereof, wherein the fluorescent dyes comprise organic dyes and/or inorganic dyes, and wherein the phosphorescent dyes comprise doped oxides, nitridesm oxynitrides, sulfides, selenides, halides, silicates, and aluminates of calcium, strontium, barium, zinc, cadmium, manganese, silicon, and rare earth metals or mixtures thereof.

15. The method according to claim 1, wherein the photoluminescent dyes comprise anti-stoke dyes.

16. The method according to claim 1, wherein a proportion of the photoluminescent dyes in the ink formulations is independently of each other 0.01 to 70.0% by weight, of the total weight of the respective ink formulation.

17. The method according to claim 1 wherein the emitted radiation gives an individual, time-dependent photoluminescence spectrum, which is detected with a spectrometer.

18. An optical, time-dependent security feature on at least one surface area of a product in the form of a multidimensional code containing two or more photoluminescent dyes that emit radiation in the range of 380-3000 nm under photon excitation and differ in their photoluminescence lifetimes, wherein the optical, time-dependent security feature is printed on at least one area of the surface of the product using the method according to claim 1.

19. The optical, time-dependent security feature according to claim 18 is used in a serialization and/or track & trace system and/or for document security.

20. A cyber-physical system (CPS) for product monitoring and/or document security comprising the optical time-dependent security feature according to claim 18.

* * * * *